United States Patent [19]

Kaiser et al.

[11] Patent Number: 5,643,316

[45] Date of Patent: Jul. 1, 1997

[54] METHOD OF THORACOSCOPIC SURGERY USING HINGED TISSUE GRASPING FORCEPS

[75] Inventors: Larry R. Kaiser, Wynnewood; William H. Pilling, North Wales, both of Pa.

[73] Assignees: The Trustees of the University of Pennsylvania, Philadelphia, Pa.; Pilling Co., Fort Washington, Pa.

[21] Appl. No.: 424,124

[22] Filed: Apr. 19, 1995

Related U.S. Application Data

[63] Continuation of Ser. No. 53,920, Apr. 27, 1993, abandoned.

[51] Int. Cl.⁶ .......................... A61B 17/06; A61B 17/28
[52] U.S. Cl. ............................................................. 606/205
[58] Field of Search ............................. 606/205–209

[56] References Cited

U.S. PATENT DOCUMENTS

| | | |
|---|---|---|
| 943,263 | 12/1909 | Moraweck . |
| 945,292 | 1/1910 | Sether . |
| 1,462,202 | 7/1923 | Hopper . |
| 2,723,666 | 11/1955 | Greenberg . |
| 2,778,357 | 1/1957 | Leibinger et al. . |
| 2,796,065 | 6/1957 | Kapp . |
| 3,608,554 | 9/1971 | McGuinness . |
| 3,921,641 | 11/1975 | Hulka . |
| 3,952,749 | 4/1976 | Fridolph et al. . |
| 4,192,313 | 3/1980 | Ogami . |
| 4,226,240 | 10/1980 | Walker, Jr. . |
| 4,226,241 | 10/1980 | Walker, Jr. . |
| 4,600,007 | 7/1986 | Lahodny et al. . |
| 4,605,002 | 8/1986 | Rebuffat . |
| 4,827,929 | 5/1989 | Hodge . |
| 5,059,214 | 10/1991 | Akropov et al. ................... 606/207 |
| 5,133,724 | 7/1992 | Wilson, Jr. et al. . |

OTHER PUBLICATIONS

"One Hundred Consecutive Patients Undergoing Video–Assisted Thoracic Operations" by The Society of Thoracic Surgeons 1992, pp. 421–426 by Lewis et al.

"Pilling Surgical Instrument Catalog", Lit. No. 99–1000, pp. 335 and 363, Pilling Co. 1993.

Primary Examiner—Michael Buiz
Assistant Examiner—Nancy Mulcare
Attorney, Agent, or Firm—Howson and Howson

[57] ABSTRACT

A method and apparatus for thoracoscopic surgery uses a hinged, ring-handled forceps having a length of approximately 12–13 inches inserted through a small incision without a cannula. Portions of the forceps extending from the hinge are straight and substantially parallel to each other when the jaws are closed. The forceps is then inserted into the patient's thoracic cavity through the incision until the hinge axis is approximately at the location of the incision. The jaws are then spread apart without significantly expanding the incision. Straight, side-curved, C-shaped and S-shaped instruments are described. Ratchet teeth disposed at a pitch of less than 0.1 inch are used to achieve small steps in jaw positioning.

3 Claims, 5 Drawing Sheets

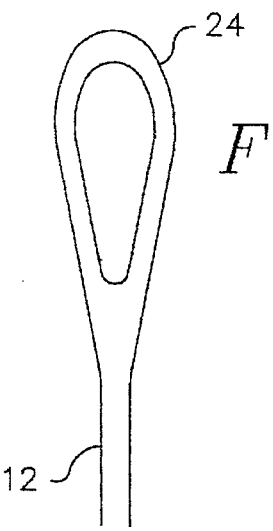
Fig. 2
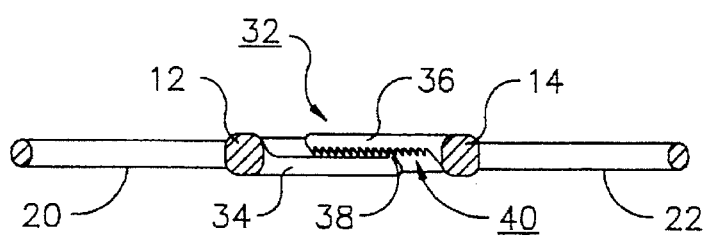
Fig. 3
Fig. 7
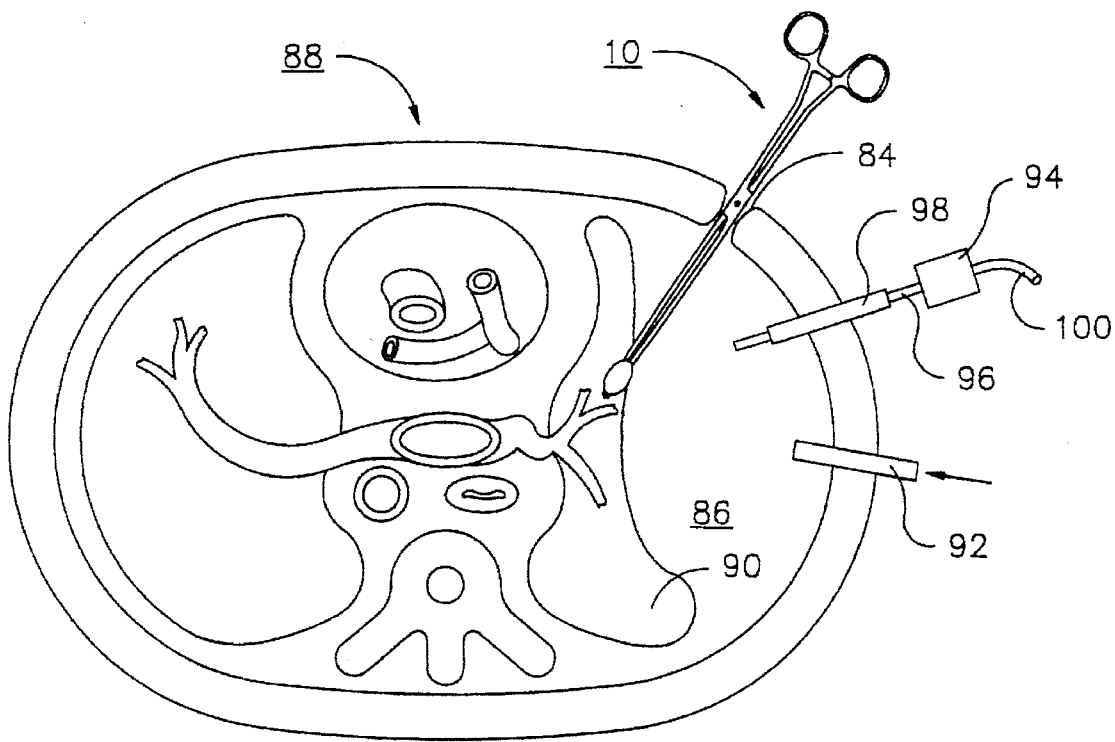

METHOD OF THORACOSCOPIC SURGERY USING HINGED TISSUE GRASPING FORCEPS

CROSS-REFERENCE TO RELATED APPLICATION

This is a continuation of my application Ser. No. 08/053,920, filed Apr. 27, 1993, now abandoned.

BRIEF SUMMARY OF THE INVENTION

This invention relates generally to surgical methods and instruments, and more particularly to tissue-grasping forceps for and method of using same in thoracic surgery in which instruments are introduced through small openings in the thoracic wall, thereby avoiding the need for making a large incision and cutting the patient's ribs.

Endoscopic techniques have been used for a number of years in thoracic surgery. Openings are made in the patient's chest wall by means of trocars. Each trocar is part of trocar/cannula combination comprising a tube (the cannula), and a cutting device (the trocar) having a sharp cutting end and removably extending through the tube. When the trocar is removed, the cannula is left in place for the duration of the surgical procedure.

Typically four holes are made. One cannula is used in conjunction with a television camera which is used to display an image of the interior of the thorax on one or more television screens for viewing by the surgical team. The camera is ordinarily located external to the patient, and the image is carried to the camera by means of an optical fiber bundle extending through the cannula. Illumination is provided by optical fibers which extend through the same cannula.

Other cannulae are used for the introduction of surgical instruments such as scissors, forceps, etc, and for the injection of gas to effect a pneumothorax (collapsed lung). The surgical instruments which are introduced through the cannulae are typically of the "endoscopic" type in which a pair of jaws, or a pair of scissor blades, are situated at the distal end of an elongated tube and manipulated by a pair of rings situated at the proximal end of the tube, one ring being connected to the tube itself, and the other being connected to a wire extending through the tube and axially movable therein. An instrument constructed in this way has a narrow profile throughout its length and is thus able to pass through the cannula, which is ordinarily not more than about one centimeter in diameter.

One problem with the multiple trocar/cannula technique is that the trocar/cannula combinations, which are disposable, are expensive. Another problem is that the cannula may cause irritation or infection in the already-compromised patient.

Accordingly, one object of this invention is to provide a forceps and method which can be used in thoracoscopic surgery without the need for a cannula. The forceps in accordance with the invention can be inserted through a small incision in the chest wall. The only trocar/cannula combinations needed are the one associated with the television camera, and the one for injection of gas, if gas injection is required.

The instrument in accordance with the invention resembles a conventional sponge forceps of the kind used to handle sponges in conventional surgery. However, the instrument in accordance with the invention is longer than a sponge forceps.

A typical sponge forceps is a box joint instrument having ring handles and a pair of jaws each of which is in the shape of a loop. It is typically 7 to 9 inches in length, and is too short to be used in the type of surgery here involved. The instrument of the invention is at least approximately 12 inches in length and not more than approximately 13 inches in length. The measurement is taken from the proximal end to the distal end of the instrument along its length. Thus, in the case of an instrument which is curved, the line of measurement is also curved.

The new instrument is used as a grasping instrument, for example, for the removal of cysts; the treatment or removal of other lesions, and in numerous other applications.

The instrument can be straight or curved in shape. The shape can be a simple gradual bend, or two bends (C-shape) or (S-shape). If the box joint is near the distal end (the jaw end), the force which can be applied by the instrument is greater. However its reach is shorter, as the box is preferably at or near the incision when the instrument is in use. If the box joint is near the proximal end (the handle end), the reach of the instrument is longer, but the force applied is less, because the leverage is less.

As in most box joint instruments, the handles are provided with overlapping projections having ratchet teeth for locking the jaws in fixed positions. In the case of an instrument having the box joint near the proximal end, the tooth pitch of the ratchet is preferably finer so that the discrete positions at which the jaws are held by the ratchet are close together. In a conventional instrument, the jaws each have four teeth. In the new instrument, especially one in which the box joint is near the proximal end, one ratchet projection has one tooth, and the other has eleven teeth.

Briefly, the objects of the invention are addressed by a hinged forceps which are directly insertable through a small incision made in the patient's chest, without the use of a cannula, and in which the length of the instrument is such as to reach various surgical sites within the patient's thorax while the hinge of the instrument is located approximately at the location of the incision. The handle can be manipulated in scissors-like fashion to cause the jaws of the forceps to open and close. More specifically, the invention comprises first and second elongated elements, each having opposite ends with a jaw formed at one end and a ring handle at the other end. The elements are hinged together at a single intermediate location between the jaw of each element and the ring handle of each element. The jaws are located at a distal end of the forceps and the ring handles are located at a proximal end of the forceps. The hinging means pivots the elements together for relative movement about a pivot axis, and constrains the jaws for movement toward and away from each other as the ring handles are moved relative to each other. The jaws being movable into engagement with each other. The forceps has a centerline extending along its length and, through the pivot axis, from the proximal to the distal end of the forceps. The first and second elements of the forceps are disposed substantially symmetrical with respect to the centerline. The forceps have an overall length between 12 and 14 inches, measured along the centerline from the distal end of the instrument, when the jaws are in engagement with each other to an imaginary line, at the proximal end of the forceps, the imaginary line being tangent to the ring handles and transverse to the centerline.

The instrument can be provided in various different configurations, for example with a straight centerline, or a centerline which is curved, either in a plane to which the pivot axis is perpendicular, or in a plane in which the pivot axis lies. The curvature can be C-shaped or S-shaped.

In a preferred embodiment of the instrument, the distance between the pivot axis and the imaginary line at the proximal end is less than the distance between the pivot axis and the distal end of the forceps. Preferably, the distance between the pivot axis and the imaginary line is approximately 5.5 inches. In the embodiment in which the pivot axis is located toward the proximal end of the instrument, the hinged elements are preferably provided with interengaging ratchet teeth approximately at the locations of said ring handles, with the ratchet teeth having a pitch of less than approximately one-tenth inch.

In the method of using the forceps, an incision is made in the chest wall of a patient. The incision is of a size just sufficient to receive the forceps when its jaws are together. With the jaws closed, the forceps is inserted through the incision until the pivot axis of the forceps is approximately at the location of the incision. Thereafter the ring handles of the forceps are manipulated to spread the jaws of the forceps. Since the pivot axis of the instrument is at or very near the incision, the instrument can be manipulated without significantly expanding the incision. Thus, it is possible to carry out thoracoscopic surgery with a hinged forceps, and to eliminate at least one cannula.

Another feature of the invention is a special configuration of the portions of the hinged elements extending from the pivot hinge to the ring handles. In a preferred embodiment of the invention, these portions extend substantially straight and parallel to each other, from the hinge to a bend location nearer to the ring handles than to the hinge, and then diverge from each other from the bend location to the ring handles. With this configuration, the portions of the hinged elements are close to each other throughout the majority of the distance from the hinge to the ring handles. This enables the jaws of the instrument to be opened and closed throughout an increased range of axial movement of the instrument.

Other objects and novel features of the invention will become more apparent from the following detailed description when considered in connection with the accompanying drawings.

BRIEF DESCRIPTION OF THE DRAWINGS

FIG. 2 is a fragmentary elevational view showing the jaws at the distal end of the forceps, as viewed from either side in FIG. 1;

FIG. 3 is sectional view taken on plane 3—3 in FIG. 1, showing ratchet teeth in the forceps of FIG. 1;

FIG. 7 is a schematic superior view of a transverse section of a supine patient, taken at a thoracic exposure, with the forceps of FIG. 1 applied through an incision into the chest cavity.

DETAILED DESCRIPTION

Figure 1:
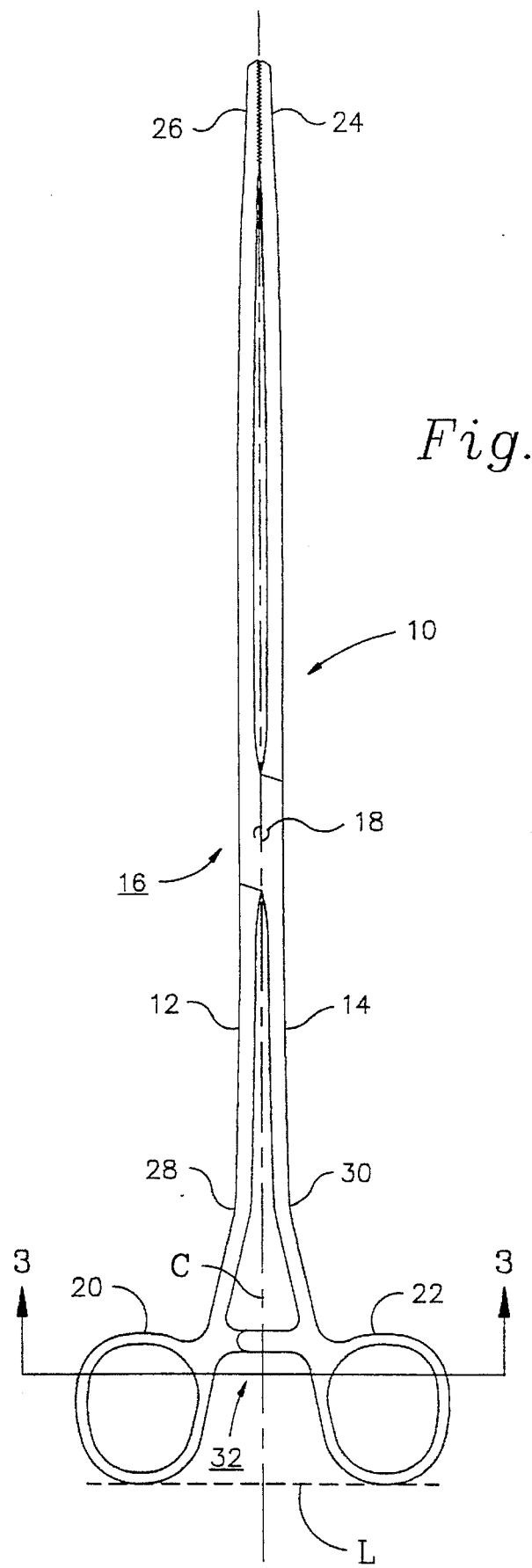
FIG. 1 is an elevational view of a straight tissue grasping forceps in accordance with a first embodiment of the invention.

FIG. 1 shows a tissue grasping forceps 10 comprising a pair of elements 12 and 14, preferably of stainless steel. These elements are hinged together by a box joint 16, such as disclosed in J. Fridolph et al. U.S. Pat. No. 3,952,749, so that they are pivotable relative to each other about a pivot axis 18.

Element 12 has a ring 20 formed at one end, and element 14 has a similar ring 22 formed at one end. These two rings, which are located opposite to each other at the proximal end of the instrument, allow the surgeon to manipulate the elements to open and close jaws 24 and 26 formed at the distal ends of elements 12 and 14 respectively. The portions of elements 12 and 14 extending from box joint 16 to the rings are bent outward at 28 and 30, near the rings. By virtue of these bends, the rings are situated far enough apart to be easily handled when the jaws are closed, and the portions of elements 12 and 14 extending from the bends to the box joint are substantially straight, and are parallel and close together when the jaws are closed, to minimize the width of the instrument.

The jaws of the instrument are preferably in the shape of a loop, as shown in FIG. 2, and are similar in shape to the jaws of a conventional sponge-grasping forceps. In order to prevent slippage and minimize trauma, the opposed faces of the jaws are preferably provided with atraumatic serrated teeth formed in accordance with U.S. Pat. No. 3,608,554.

Referring again to FIG. 1, the overall length of the instrument, measured from the distal end (the jaw end), when the jaws are together, to an imaginary transverse line L tangent to both rings at the proximal end of the instrument, is between approximately 12 and 13 inches.

This measurement is taken along an imaginary centerline C, which passes through pivot axis 18 and with respect to which both elements 12 and 14 are substantially symmetrical. Hinge 16 is positioned so that the pivot axis 18 of the instrument is located closer to the proximal end of the instrument, preferably about 5.5 inches from line L and 6.5 to 7.5 inches from the distal end of the instrument. The positioning of the pivot axis nearer to the proximal end than to the distal end places the pivot axis at, or in the vicinity of, the incision during surgery, and makes it possible to operate the instrument without expanding the small incision through which it is inserted, and to reach easily various anatomical structures within the patient's thoracic cavity.

Adjacent to the rings, the elements are provided with a ratchet 32, best shown in FIG. 3. The ratchet comprises a pawl 34 extending from element 12 and a rack 36 extending from element 14 and overlying pawl 34. A tooth 38 is formed at the end of pawl 34 remote from element 28, and the tooth is engageable with any one of rack teeth 40 to lock elements 12 and 14 against separating movement relative to each other. The teeth are shaped to allow the elements to move toward each other when the rings are squeezed, but to require opposite forces to be applied to the rings in the vertical direction in FIG. 3, so that pawl 34 is disengaged from teeth 38, in order to move elements 12 and 14 apart from each other.

Unlike the ratchets in conventional ring-handle forceps and clamps, which typically consist of two elements each having four teeth with a pitch distance of around 0.2 inch., ratchet 32 comprises a pawl with a single tooth 38, and a rack 36 with teeth 40 disposed at a pitch distance of less than approximately 0.1 inch, preferably 0.093 inch. The small pitch distance makes it possible to adjust the relative positions of the jaws 24 and 26 in small steps, even though the hinge of the instrument is located nearer to the proximal end than to the distal end.

Figure 4:
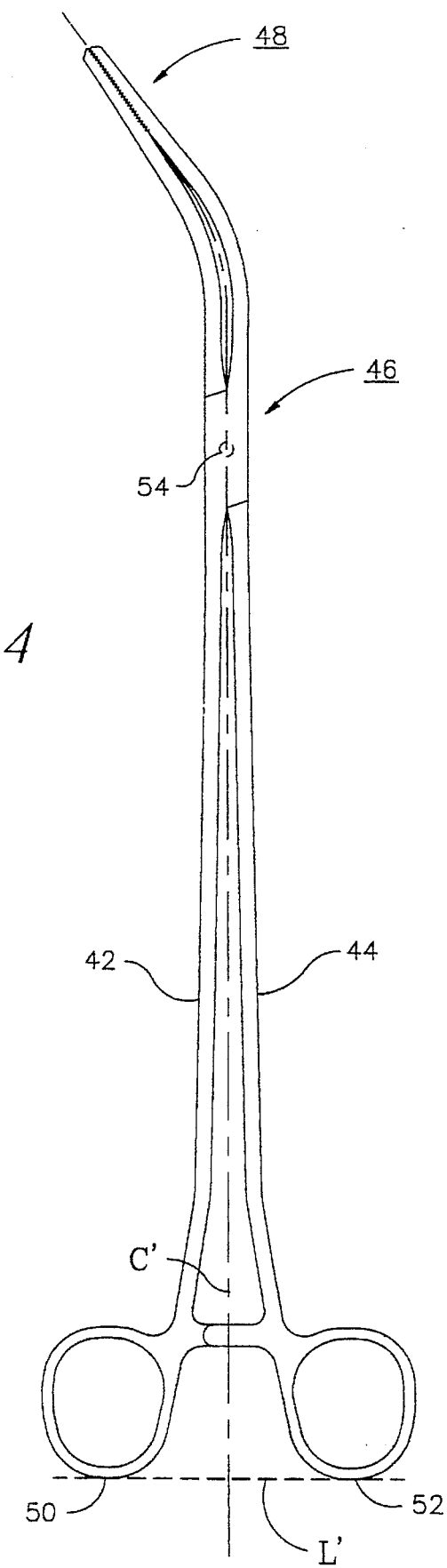
FIG. 4 is an elevational view of a side curved forceps in accordance with a second embodiment of the invention.

In the side-curved instrument of FIG. 4, two elements 42 and 44 are hinged together by box joint 46, which is located nearer to the jaws 48 at the distal end than to the rings 50 and 52 at the proximal end. The centerline C' of the instrument is substantially straight from the imaginary proximal tangent line L' to pivot axis 54, but the portion extending from pivot axis 54 to the distal end of the instrument is curved to the side. Here again the two elements 42 and 44 are symmetrical with respect to the centerline. The centerline lies in a plane to which the pivot axis is perpendicular. Here again, the length of the instrument, measured along centerline C', from the distal end to line L' at the proximal end, is in the range of approximately 12 to 13 inches.

Figure 5:
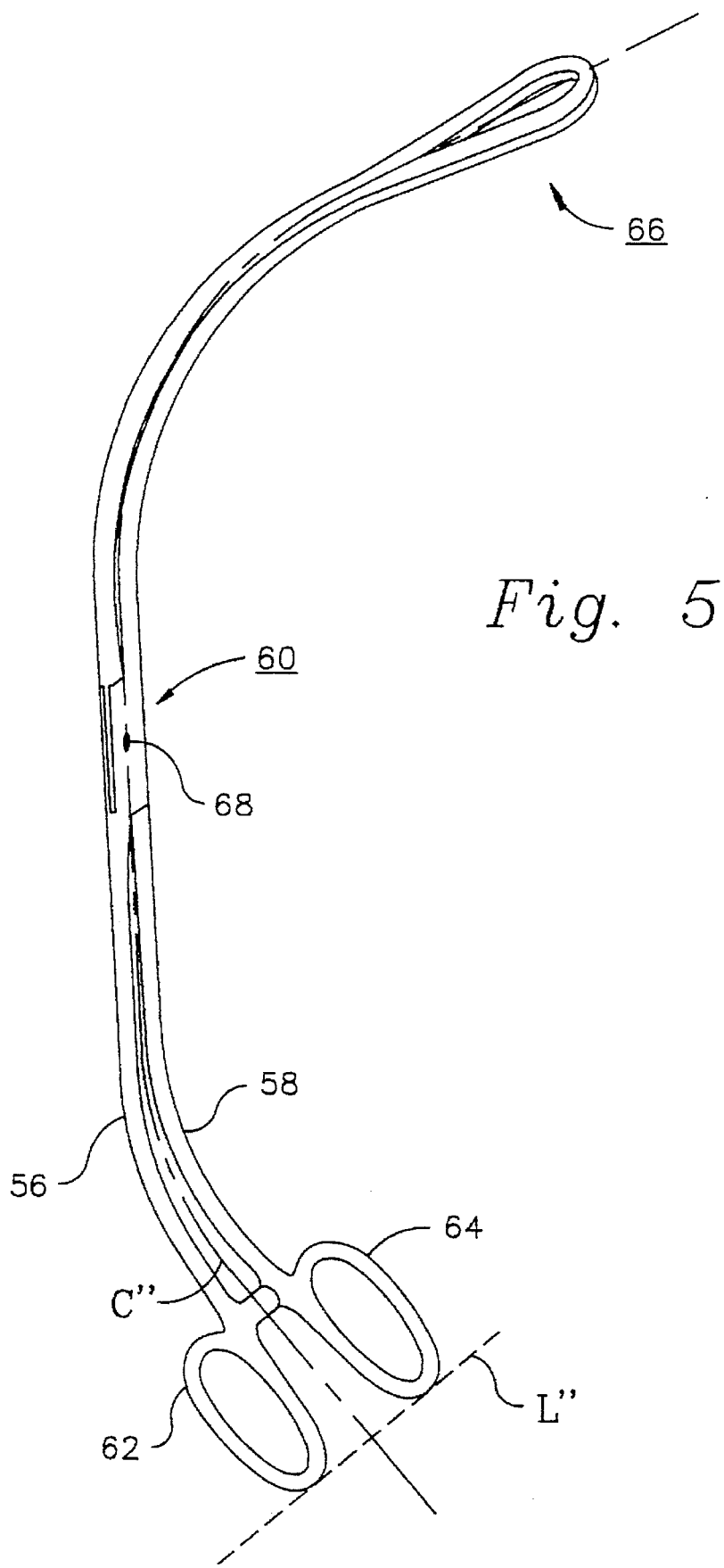
FIG. 5 is a perspective view of a C-shaped curved forceps in accordance with a third embodiment of the invention.

In the C-shaped instrument of FIG. 5, two elements 56 and 58 are hinged together by box joint 60, which is located nearer the rings 62 and 64 at the proximal end than to the jaws 66 at the distal end. The centerline C'' of the instrument is C-shaped. The portion of centerline C'' from the imaginary proximal tangent line L'' to pivot axis 68 is curved, as is the portion extending from the pivot axis to the distal end. An intermediate portion of the centerline, extending through the pivot axis, is straight. The centerline lies substantially entirely in a plane in which the pivot axis lies. Here again, the two elements 56 and 58 are symmetrical with respect to the centerline. The overall length of the instrument, measured along centerline C'', from the distal end to line L'' at the proximal end, is in the range of approximately 12 to 13 inches. The distance from the pivot axis to line L'' to the proximal end is approximately 5.5 inches, measured along the centerline.

Figure 6:
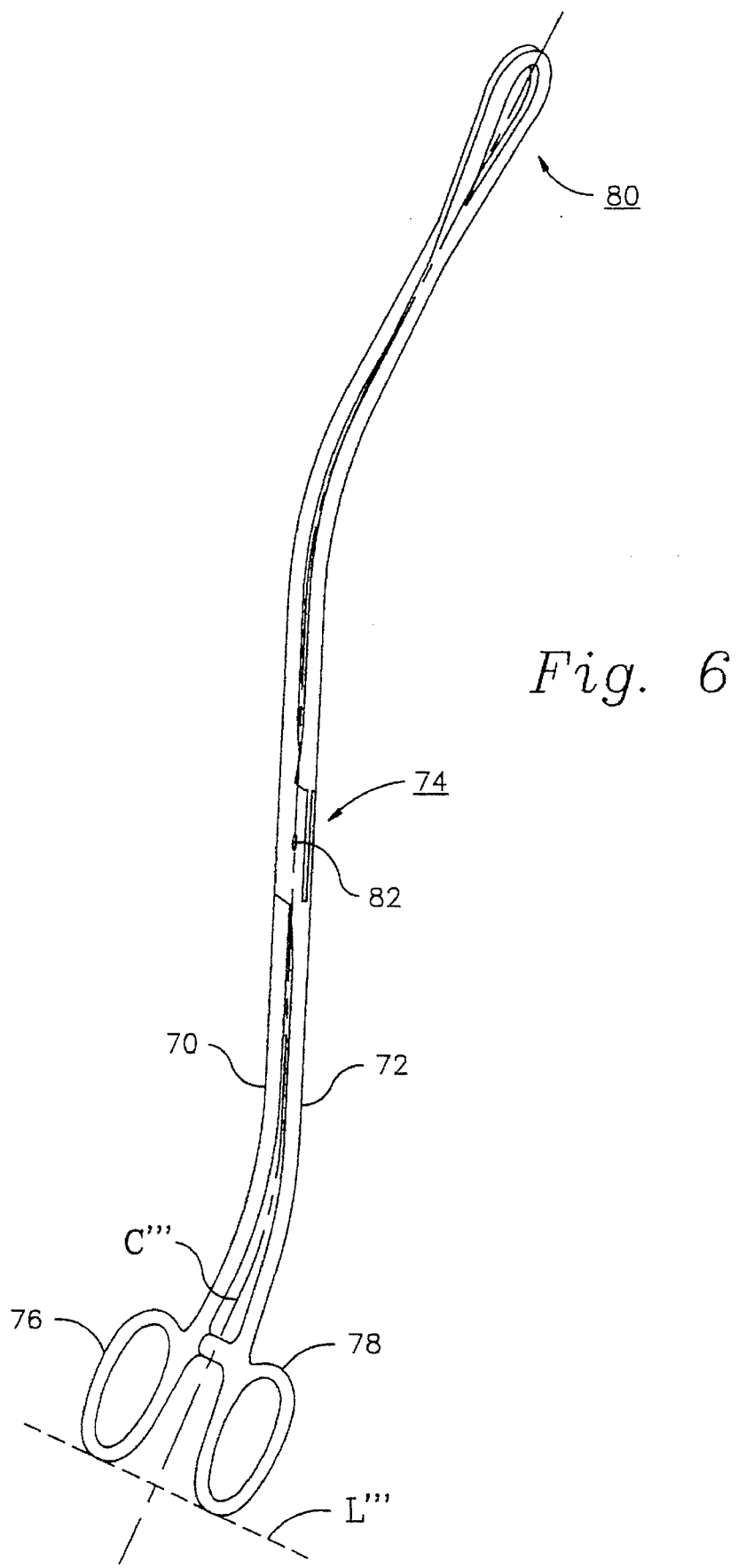
FIG. 6 is a perspective view of an S-shaped curved forceps in accordance with a fourth embodiment of the invention.

In the S-shaped instrument of FIG. 6, two elements 70 and 72 are hinged together by box joint 74, which is located nearer to the rings 76 and 78 at the proximal end than to the jaws 80 at the distal end. The centerline C''' of the instrument is S-shaped. The portion of centerline C''' from the imaginary proximal tangent line L''' to pivot axis 82 is curved, as is the portion extending from the pivot axis to the distal end. An intermediate portion of the centerline, extending through the pivot axis, is straight. The centerline lies substantially entirely in a plane in which the pivot axis lies. Here again, the two elements 70 and 72 are symmetrical with respect to the centerline. The overall length of the instrument, measured along centerline C''', from the distal end to line L''' at the proximal end, is in the range of approximately 12 to 13 inches. The distance from the pivot axis to line L''' to the proximal end is approximately 5.5 inches, measured along the centerline.

The manner in which the forceps 10 is used in thoracoscopy is illustrated in FIG. 7. An incision 84 is made in the chest wall of the patient just sufficient in size to receive the forceps 10 when its jaws 24 and 26 are together. With the jaws closed, forceps 10, is inserted through incision 84 into the thoracic cavity 86 of a patient 88 until the pivot axis 18 of forceps 10 is approximately at the location of incision 84. Forceps 10 can then be moved axially inward or outward, and the jaws 24 and 26 can be operated without substantially expanding incision 84. The right lung 90 is partially collapsed by the pressure of gas introduced through a cannula 92. The surgical site within the thoracic cavity is viewed by means of a television camera 94, which receives an optical image by means of an optical fiber bundle 96 having suitable image forming optics at its distal end. The fiber bundle also conducts light from an external light source to the interior of the thoracic cavity to illuminate the surgical site. The fiber bundle extends through a cannula 98. The television camera is connected by means of an electrical cable 100 to one or more television monitors (not shown) in the operating room to allow the surgical team to observe the operation in detail as it takes place within the interior of the patient's thorax.

The instruments of FIGS. 1, 5 and 6 can be used to reach various locations within a patient's thoracic cavity, the choice of a particular instrument depending on the particular location to be reached. When the jaws of the instrument are opened and closed, ideally the box joint should be located within the incision in the patient's chest wall. However, it is possible to move the instrument inward or outward somewhat from the ideal position and still operate the jaws, since the relatively movable elements of the instrument remain close to each other in the vicinity of the box joint.

The instrument of FIG. 4, which has its box joint nearer to the distal end than to the proximal end can be used where the anatomical structure to be grasped by the jaws is located near the incision through which the instrument is introduced. The jaws of this instrument, of course, are capable of applying a greater force than the jaws of the instruments of FIGS. 1, 5 and 6.

Of course, in a thoracoscopic surgical procedure, it is possible to withdraw one of the instrument shown, and to introduce another instrument through the same incision. As will be apparent from the foregoing description, with the forceps constructed in accordance with this invention, it is possible to eliminate at least one trocar/cannula combination, to reach various anatomical structures within a patient's thoracic cavity, and to carry out thoracoscopic surgery more easily than was heretofore possible.

The bends at 28 and 30, as shown in FIG. 1 allow the hinged elements to be close to each other throughout most of the length of the instrument when the jaws are closed. Because they increase the axial range of the instrument, they are applicable to instruments which are somewhat shorter than 12 inches in length.

Various modifications can be made to the instruments herein described. For example, while the loop-shaped jaw configuration is desirable, other jaw configurations can be used. In instruments which are to be used strictly as grasping forceps, and which do not require a clamping capability, the ratchet can be eliminated. Other modifications, which will occur to persons skilled in the art, can be made without departing from the scope of the invention, as defined in the following claims.

We claim:

1. A method of thoracoscopic surgery using forceps comprising a pair of elements connected at a hinge and having proximal and distal ends, with handles at the proximal ends of the elements and cooperating jaws at the distal ends of the elements, in which portions of the elements extending from the hinge to locations in the proximal direction from the hinge are substantially parallel to each other when the jaws are together, comprising the steps of:

making an incision in the chest wall of a patient just sufficient in size to receive the forceps when the jaws are together;

inserting the forceps through said incision to a position where the hinge is approximately at the location of the incision but inside the patient and said portions of the elements extend through the incision; and operating the handles to spread the jaws of the forceps apart from each other while said portions of the elements extend through said incision, whereby the jaws are spread apart without substantially expanding the incision.

2. A method of thoracoscopic surgery using forceps comprising a pair of elements connected at a hinge and having proximal and distal ends, with handles at the proximal ends of the elements and cooperating jaws at the distal ends of the elements, in which portions of the elements extending from the hinge to locations in the proximal direction from the hinge are substantially parallel to each other when the jaws are together, and in which portions of the elements extending in the proximal direction from said locations diverge from each other when the jaws are together comprising the steps of:

making an incision in the chest wall of a patient just sufficient in size to receive the forceps when the jaws are together;

inserting the forceps through said incision to a position where the hinge is approximately at the location of the incision but inside the patient and said portions of the elements which are substantially parallel to each other when the jaws are together extend through the incision; and operating the handles to spread the jaws of the forceps apart from each other while said portions of the elements which are substantially parallel to each other when the jaws are together extend through said incision, whereby the jaws are spread apart without substantially expanding the incision.

3. A method of thoracoscopic surgery using forceps comprising a pair of elements connected at a hinge and having proximal and distal ends, with handles at the proximal ends of the elements, cooperating jaws at the distal ends of the elements, and ratchet means adjacent to the handles for limiting separating movement of the jaws relative to each other, in which portions of the elements extending in the proximal direction from the hinge to intermediate locations between the hinge and the ratchet means are substantially parallel to each other when the jaws are together, said intermediate locations being closer to the ratchet means than they are to the hinge, and in which portions of the elements extending in the proximal direction from said locations diverge from each other toward the ratchet means when the jaws are together, comprising the steps of:

forming an incision in the chest wall of a patient just sufficient in size to receive the forceps when the jaws are together;

inserting the forceps through said incision to a position where the hinge is approximately at the location of the incision but inside the patient and said portions of the elements which are substantially parallel to each other when the jaws are together extend through the incision; and operating the handles to spread the jaws of the forceps apart from each other while said portions of the elements which are substantially parallel to each other when the jaws are together extend through said incision, whereby the jaws are spread apart without substantially expanding the incision.

* * * * *